(12) United States Patent
Meneghin et al.

(10) Patent No.: US 8,181,491 B2
(45) Date of Patent: May 22, 2012

(54) PROSTHETIC KNIT FOR TREATING PROLAPSES

(75) Inventors: Alfredo Meneghin, Lyons (FR); Michel Therin, Lyons (FR); Linda Spinnler, Villefranche sur Saone (FR); Julie Lecuivre, Villefranche sur Saône (FR)

(73) Assignee: Sofradim Production, Trevoux (FR)

( * ) Notice: Subject to any disclaimer, the term of this patent is extended or adjusted under 35 U.S.C. 154(b) by 1133 days.

(21) Appl. No.: 12/070,260

(22) Filed: Feb. 15, 2008

(65) Prior Publication Data

US 2008/0208360 A1 Aug. 28, 2008

Related U.S. Application Data

(60) Provisional application No. 60/901,380, filed on Feb. 15, 2007.

(51) Int. Cl.
*D04B 21/00* (2006.01)

(52) U.S. Cl. .......................................... 66/195; 66/202

(58) Field of Classification Search ............ 66/191–195, 66/202, 198; 606/151
See application file for complete search history.

(56) References Cited

U.S. PATENT DOCUMENTS

| | | | | |
|---|---|---|---|---|
| 4,633,873 A * | 1/1987 | Dumican et al. | ............. | 606/151 |
| 4,769,038 A | 9/1988 | Bendavid et al. | | |
| 6,971,252 B2 * | 12/2005 | Therin et al. | .................. | 66/170 |
| 7,156,858 B2 * | 1/2007 | Schuldt-Hempe et al. | ... | 606/151 |
| 7,290,410 B2 * | 11/2007 | Meneghin et al. | ............. | 66/195 |
| 2003/0100954 A1 | 5/2003 | Schuldt-Hempe et al. | | |
| 2004/0034373 A1 | 2/2004 | Schuldt-Hempe et al. | | |
| 2005/0070930 A1 * | 3/2005 | Kammerer | .................... | 606/151 |
| 2006/0281967 A1 * | 12/2006 | Meneghin et al. | ............. | 600/37 |
| 2008/0127682 A1 * | 6/2008 | Meneghin et al. | ............. | 66/170 |
| 2008/0208360 A1 * | 8/2008 | Meneghin et al. | ......... | 623/23.75 |
| 2009/0318752 A1 * | 12/2009 | Evans et al. | .................... | 600/37 |
| 2009/0326565 A1 * | 12/2009 | Trabucco et al. | ............ | 606/151 |

(Continued)

FOREIGN PATENT DOCUMENTS

FR 2 244 853 4/1975

(Continued)

OTHER PUBLICATIONS

French Search Report from French Application No. FR 0701109 dated Oct. 11, 2007.

*Primary Examiner* — Danny Worrell
(74) *Attorney, Agent, or Firm* — Carter, DeLuca, Farrell & Schmidt, LLP (57) ABSTRACT

The present invention relates to a prosthetic open knit fabric (10) made as a single piece, based on an arrangement consisting of several sets of yarns of a biocompatible polymer material, comprising, continuously in the direction of production of the knit, a central strip (11) and two lateral strips (12), one on each side of the central strip, characterized in that it comprises one or more set(s) of pillar stitch yarns defining a pillar stitch pattern, the said one or more set(s) of pillar stitch yarns extending across the entire width of the central strip (11) and of the lateral strips (12) and together forming a first threading across the width of the central strip and a second threading across the width of the lateral strips, the said first and second threading being different, and at least two partial weft stitching sets.

The present invention also relates to a method of producing such a knit fabric and to an implant for supporting prolapses obtained from such a knit fabric.

32 Claims, 3 Drawing Sheets

U.S. PATENT DOCUMENTS

| | | | |
|---|---|---|---|
| 2011/0190571 A1* | 8/2011 | Deegan | 600/30 |
| 2011/0190573 A1* | 8/2011 | Deegan | 600/37 |

FOREIGN PATENT DOCUMENTS

| | | | |
|---|---|---|---|
| FR | 2 859 624 | | 3/2005 |
| FR | 2 863 277 | | 6/2005 |
| FR | 2 844 706 | | 10/2006 |
| FR | 2884706 | A1 * | 10/2006 |
| FR | 2884835 | A1 * | 10/2006 |
| FR | 2912761 | A1 * | 8/2008 |

* cited by examiner

PROSTHETIC KNIT FOR TREATING PROLAPSES

CROSS REFERENCE TO RELATED APPLICATIONS

The present application claims the benefit of and priority to provisional application Ser. No. 60/901,380 filed on Feb. 15, 2007, the entire contents of which is incorporated by reference herein.

The present invention relates to a prosthetic knit fabric with mechanical strength and elasticity both of which can vary, in at least one dimension or direction of the said knit fabric, and which can be used in particular in the form of supports equipped with suspender arms or slings, cut from the said knit fabric, for treating disorders of the pelvic floor, mainly in women, also known as prolapses.

Prolapses is a phenomenon that affects an organ or part of an organ that protrudes, for example at the vaginal wall. The protruding organs may be the uterus, the bladder, the rectum and the small intestine. The present invention deals in particular with the treatment of prolapses of the genital tracts in women occurring at the anterior or posterior wall of the vagina, also known as cystocele and rectocele.

Surgical treatment of prolapses entails the use of reinforcements in the form of implants for supporting the prolapsed organ. The central part of the implant is positioned at this organ and may be in contact with the latter in order to support it, while the lateral parts of the implant, generally in the form of suspender arms or slings, are fixed to stable anatomical elements such as the abdominal wall, the obturating membrane, the sacral bone, the sacrosciatic ligaments or the elevator muscles of the anus, for example by means of clips, anchors, sutures or simply by anchoring into the tissue.

In the known way, a supporting implant such as this must meet numerous requirements, and in particular must have suitable mechanical strength in all directions, must be biocompatible, flexible, but nonetheless exhibit a certain degree of elasticity. These supporting implants have preferably to be macroporous and non-aggressive in their central part that supports the organ. These supporting implants have also to be capable of being sutured. Finally, it is desirable for these supporting implants to be tailored to the build of the patient.

The shaping of textiles in order to tailor them, on the one hand, to suit the anatomy of the sub-urethral region and, on the other hand, to the surgical technique employed, is known.

Surgical techniques for treating prolapses are increasingly having recourse to reinforcements that exhibit a central region, that is positioned under the organ that is to be supported, that is wider than the lateral ends which are intended to be anchored some distance away into the musculoaponeurotic elements. The functions of these two regions thus tend to be specialized: flexible and comfortable support under the organ, and suspension and anchoring laterally.

Figure 1:
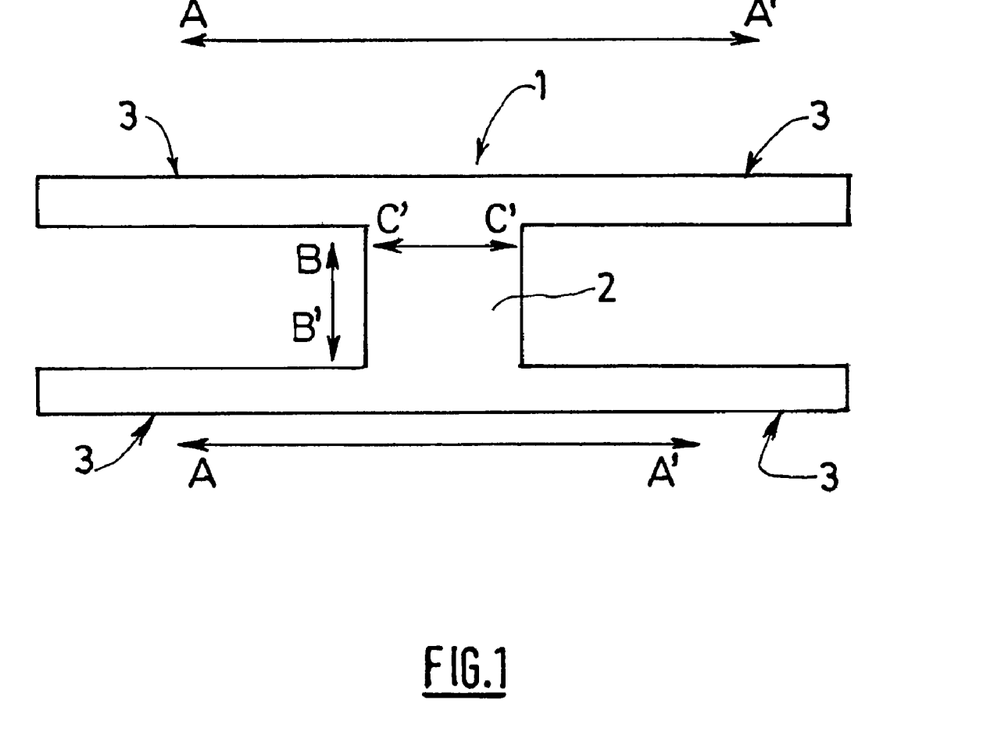
FIG. 1 depicts an implant of the prior art for treating a prolapse of the cystocele type.
Figure 2:
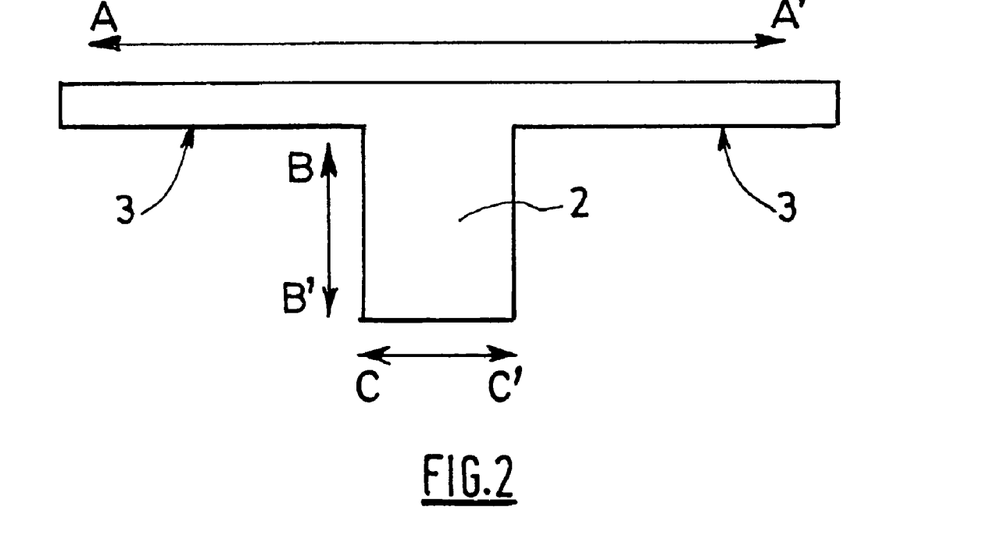
FIG. 2 depicts an implant of the prior art for treating a prolapse of the rectocele type.

Examples of forms of reinforcements of the prior art are shown in FIGS. 1 and 2.

FIG. 1 depicts an example of a reinforcement 1 for treating a prolapse such as cystocele. The central part 2 of the reinforcement 1 has the overall form of a quadrilateral. This central part 2 is intended to be positioned under the organ that is to be supported, for example the bladder. The reinforcement also has four extending or suspender arms 3 intended to be fixed for example to the obturating membrane. AA' defines the longitudinal direction of the extending arms 3, and BB' defines the longitudinal direction of the central part 2 or support. CC' defines the transverse direction of the central part 2 or support.

FIG. 2 depicts an example of a reinforcement 1 for treating a prolapse such as rectocele. The central part 2 of the reinforcement has the overall shape of a quadrilateral. This central part is intended to be positioned under the organ that is to be supported, for example the rectum. The reinforcement 1 also has two extending or suspender arms 3 which are intended to be fixed for example at the sacrosciatic ligaments or elevator muscles. AA' defines the longitudinal direction of the extending arms 3 and BB' defines the longitudinal direction of the central part 2 or support. CC' defines the transverse direction of the central part 2 or support.

The mechanical and biological properties expected of these separate parts are different.

At their extending arms, these supporting implants need to have mechanical properties, particularly strength properties, which are sufficient, especially in their longitudinal direction AA'. Indeed the extending arms must not break when they are inserted and pulled into place by the surgeon and while they are supporting the prolapsed organ. In addition, in order to make it easier to adjust the tension while at the same time maintaining their shape, it is advantageous for these to be relatively resistant to longitudinal deformation.

By contrast, in the central part of the implant, which is the part that supports the prolapsed organ, it is particularly important for the implant to have minimum density, maximum porosity, great flexibility and elasticity tailored to the host tissue, particularly in the longitudinal direction BB', as depicted in FIGS. 1 and 2 of this central part. This is because since this central part is liable to find itself in contact with the organ that is to be supported, it has preferably not to be overly aggressive towards the wall of the hollow viscera such as the bladder, the vagina, the rectum or the uterus, so as to minimize risks of erosion. The central part has preferably to be flexible and elastic so as to match the compliance and elasticity of the organ that is to be supported and of the vaginal wall.

Finally, patients all have different builds and so it is important for the surgeon to be able to fashion the implant on the site where he is performing the operation, at the time of the intervention, so as to be able to tailor its configuration or shape to that of the patient's body.

Thus, it would be advantageous to be able to source a knit fabric, possibly one that can be cut on demand, that has a particularly elastic region with wide pores, and which is flexible, which could correspond to the central part of the implant, and particularly strong regions which could correspond to the extending arms of the implant.

A "stitching set of yarns" according to this application, in particular regarding a textile or a knit fabric, is to be understood as meaning a set of yarns in which the pattern chart used for knitting the yarns leads to the formation of stitches.

Document WO 01/80773 describes a prosthetic open knit fabric the central part of which has greater elasticity than the peripheral parts, the central part being intended to be deformed in order to form a protrusion. However, this knit fabric is produced in an arrangement of several sets of yarns, only one of which makes stitches, the latter being a pillar stitch pattern. The knit fabric described in WO 01/80773, because it comprises just one stitching set of yarns in the form of a pillar stitch pattern, is unbalanced and does not allow narrow parts, for example with widths of 1 cm, which have tensile strength and cannot be unravelled, to be cut from its peripheral parts.

Document WO 2005/027786 describes a prosthetic open knit fabric comprising a central strip and lateral strips with different elasticity and different mechanical strength. However, the knit fabric described in WO 2005/027786 comprises no stitching set of yarns defining a pillar stitch pattern. Thus, a knit fabric such as this has strength that is relatively uniform across the entirety of the central strip and of the lateral strips.

The present invention aims to solve this problem by proposing, in general, a knit fabric with elasticity and mechanical strength both of which vary in at least one direction or dimension of the said knit fabric, that is ready to be cut, and is particularly useful in producing or obtaining, simply and quickly, supporting implants for treating prolapses, comprising a central strip, in the direction of production of the knit, that has great elasticity and great flexibility, and two lateral strips, one on each side of the central strip, each having good tensile strength, particularly in the longitudinal direction of the knit fabric, this knit fabric being produced as a single piece and having no additional thickness or discontinuity from one strip to the other and also allowing extending arms to be cut in the form of narrow slings.

The present invention relates to a prosthetic open knit fabric made as a single piece, based on an arrangement consisting of several sets of yarns of a biocompatible polymer material, comprising, continuously in the direction of production of the knit fabric, a central strip and two lateral strips, one on each side of the central strip, characterized in that it comprises one or more set(s) of pillar stitch yarns defining a pillar stitch pattern, the said one or more sets of pillar stitch yarns extending across the entire width of the central strip and of the lateral strips and together forming a first threading across the width of the central strip and a second threading across the width of the lateral strips, the said first and second threadings being different, and at least two partial weft stitching sets of yarns.

By "partial weft stitching set of yarns", is meant according to the present invention, a weft set of yarns, i.e., yarns that move perpendicularly to the longitudinal direction EE' of the knit fabric as defined hereinbelow, said yarns forming a stitch from time to time, for example forming a stitch every 4 courses.

By "threading" on a knit fabric zone, is meant according to the present invention, the number and the distribution of yarns feeding the eyelets of the guide bars used for producing said knit fabric zone. Thus, the higher the number of eyelets fed by a yarn on one knit fabric zone, the denser the threading of said knit fabric zone.

The present invention also relates to a method of producing a prosthetic open knit fabric made as a single piece, based on an arrangement consisting of several sets of yarns of a biocompatible polymer material, comprising, continuously in the direction of production of the knit fabric, a central strip and two lateral strips, one on each side of the central strip, characterized in that it comprises the following step:

producing a knit fabric on a warp knitting machine or Raschel knitting machine in one or more sets of pillar stitch yarns (A) defining a pillar stitch pattern, the said one or more set(s) of pillar stitch yarns being threaded continuously or partly threaded across the entire width of the lateral strips and of the central strip on one or more guide bar(s) and together forming a first threading across the width of the central strip and a second threading across the width of the lateral strips, the said first and second threadings being different, and at least two additional sets of yarns (C, D), each of the additional sets being obtained from a guide bar, the pattern chart used for knitting the yarns (C, D) of each additional set leading to a partial weft stitching pattern.

The present invention further relates to a supporting implant for treating prolapses obtained by cutting a prosthetic knit fabric as described hereinabove.

The knit fabric according to the invention allows supporting implants that have a particularly elastic central part and extending arms with particularly good tensile strength to be cut easily. In particular, in the case of the implant according to the invention, the central support is cut from the central strip of the knit fabric according to the invention, the extending arms being cut from the lateral strips, in the longitudinal direction of the knit fabric, and therefore in the direction of the warp of the knit fabric.

Thus, the extending arms are continuous from one end to the other and consist across their entire length of the same knit pattern: furthermore, since this knit pattern is that corresponding to the lateral strips, the extending arms, on the one hand, have particularly good tensile strength and, on the other hand, have rather low elongation at break or extensibility.

Specifically, because there are two different threadings of the pillar stitch yarns, namely a first threading across the width of the central strip and a second threading, particularly a reinforced one and thus denser than the first threading, across the width of the lateral strips, these lateral strips in their longitudinal direction have excellent mechanical strength. Thus, the extending arms of the implant according to the invention, when cut in the longitudinal direction of the lateral strips of the knit fabric according to the invention, also have a high breaking strength: the risks of these extending arms breaking while the implant is in place are thus avoided. The lateral strips of the knit fabric according to the invention and the extending arms of the implant according to the invention thus have a dense and blocked structure. Thus, during placement of the implant, all the stresses are borne by the extending arms of the implant rather than by its central support. This allows the implant to be deployed far more precisely without introducing tension into the supporting region which lies facing the central support of the implant.

In addition, the first threading, particularly a lightened one, of the pillar stitch pattern in the central strip makes it possible to obtain a central strip that is particularly elastic and open and therefore an implant central support that is also particularly elastic and open.

In one embodiment of the knit fabric of the invention, the second threading is denser than the first threading.

In one embodiment of the invention, the knit fabric comprises two sets of pillar stitch yarns, a first set of pillar stitch yarns (A) and a second set of pillar stitch yarns (B), the said first set of pillar stitch yarns extending across the entire width of the central strip and of the lateral strips, the said second set of pillar stitch yarns extending only across the width of each of the lateral strips.

Thus, the pillar stitch pattern of the knit fabric is particularly reinforced across the width of the lateral strips, giving these greater tensile strength, and is lighter on the central strip, giving the latter elasticity and lightness of weight.

In one embodiment of the invention, the said two partial weft stitching sets of yarns extend across the entire width of the central strip and of the lateral strips of the knit fabric.

The knit fabric according to the invention is thus particularly balanced and dimensionally stabilized across its entire surface, that is to say that it does not carry any risk of losing its minimum elasticity and strength qualities in any direction or dimension whatsoever: longitudinal, transverse or diagonal, or for any strip: central or lateral, after cutting.

Furthermore, the knit fabric according to the invention is made as a single piece and has no additional thickness or discontinuity of appearance from one strip to another.

In the present application, "prosthetic knit fabric" is to be understood as meaning a knit fabric intended to be implanted in a human or animal body in the form of a prosthesis or of an implant or of any other component at least partially fashioned from the said knit fabric.

In the present application, "open knit fabric" is to be understood as meaning a knit fabric in which the pattern or patterns determine cells or voids within the knit, these cells or voids constituting passages that open at each side of the knit. An open knit fabric such as this allows for better tissue integration. In particular, because of the special way in which it is knitted, the prosthetic knit fabric according to the invention is open across all of its central and lateral strips. In particular, the porosity of the knit fabric in the central strip is greater than the porosity of the knit fabric in each of the lateral strips.

In the present application, as far as the knit fabric according to the invention or the implant according to the invention is concerned:
- the breaking load and the elongation at break in the longitudinal direction are measured in accordance with ISO 13934-1 in which the width corresponds to the width of the lateral strip, namely about 1 cm, and the length of the test specimen is 100 mm,
- the breaking load and the elongation at 30 N in the transverse direction are measured in accordance with ISO 13934-1 in which the width is 40 mm and the length of the test specimen is 60 mm.

In one embodiment of the invention, the breaking load of the knit fabric in the longitudinal direction for each lateral strip is greater than or equal to 50 N. Preferably, the said breaking load ranges from 70 to 90 N.

In one embodiment of the invention, the elongation at break of the knit fabric in the longitudinal direction for each lateral strip ranges from 25% to 70%. Preferably, the said elongation at break ranges from 50% to 70%.

In one embodiment of the invention, the breaking load of the knit fabric in the transverse direction for the central strip is greater than or equal to 60 N. Preferably, the said breaking load ranges from 70 to 90 N.

In one embodiment of the invention, the elongation at 30 N of the knit fabric in the transverse direction for the central strip ranges from 30% to 50%. Preferably, the said elongation ranges from 40% to 50%.

In one embodiment of the invention, the said central strip comprises pores the mean width of which varies from 2.5 mm to 3 mm and the mean height of which varies from 1.6 mm to 1.9 mm.

In one embodiment of the invention, the said knit fabric is based on yarns, monofilaments or multifilaments of a biocompatible polymer material chosen from polypropylene, polyester, polyamide and blends thereof. For example, the said knit fabric may be made of monofilament yarns of polypropylene having a mean diameter varying from 0.08 to 0.12 mm.

In one embodiment, the said knit fabric may further comprise other sets of yarns in addition to the set or sets of pillar stitch yarns and in addition to the two partial weft stitching sets of yarns.

In one embodiment, the said central strip is covered on at least one side with a bioresorbable material.

In one embodiment of the invention, the said knit fabric further comprises at least one radiopaque yarn. This radiopaque yarn may be chosen from biocompatible metal yarns, biocompatible polymer yarns impregnated with barium sulphate. Examples of biocompatible metal yarns include yarns made of metals chosen from platinum, platinum-iridium, titanium, steel, silver and mixtures thereof.

By virtue of the particular properties of, on the one hand, the central strip of the knit, namely elasticity and flexibility, and, on the other hand, its lateral strips, namely breaking strength, it is possible, in particular for the surgeon, to cut directly from this knit fabric a supporting implant for treating prolapses which, in its central support, has elasticity and flexibility and in its extending arms has tensile strength.

In one embodiment of the invention, the knit fabric according to the invention can be knitted directly to the desired dimensions of the supporting implant. Thus, the lateral strips of the knit fabric according to the invention correspond to the extending arms of the implant and the central strip is cut to the desired dimensions for the central support of the implant.

In one embodiment of the invention, use is made of two sets of pillar stitch yarns, a first set of pillar stitch yarns (A) and a second set of pillar stitch yarns (B), the said first set of pillar stitch yarns being threaded continuously along a first guide bar across the entire width of the lateral strips and of the central strip and the said second set of pillar stitch yarns being partly threaded on a second guide bar across only the width of each of the lateral strips.

In another embodiment of the invention, when the width of the warp knitting machine or Raschel knitting machine allows several knit fabrics to be knitted side by side, a lateral strip of a first knit fabric lies adjacent to a lateral strip of a second knit fabric so the partial weft stitching sets of the said first and second knit fabrics have a pattern such that for any pillar stitch yarn (A1) separating two adjacent lateral strips, any weft yarn of the said partial weft stitching sets approaching the said pillar stitch yarn (A1) makes a U-turn at this pillar stitch yarn (A1).

It is thus possible to obtain a supporting implant for treating prolapses by unravelling the pillar stitch yarns (A1) of such knit fabrics then cutting the central strip of the said knit fabric or knit fabrics. The unravelled lateral strips of the knit fabric constitute the extending arms of the implant while the central support of the implant is cut from the central strip of the knit fabric.

The production of such a knit fabric comprising unravellable pillar stitch yarns is described in applications WO 2006/111664 and WO 2006/111665.

This method of unravelling may also be applied to the separation of several knit fabrics according to the invention which are knitted side by side on the same knitting machine and separated from one another by unravellable pillar stitch yarns.

An unravelling method such as this makes it possible to obtain extending arms the edges of which are scalloped and do not fray. Furthermore, an unravelling method such as this is particularly economical, repeatable and reliable: specifically, it allows one of the dimensions of the implant to be obtained directly.

The present invention also relates to a supporting implant for treating prolapses, characterized in that the said extending arms are cut in the longitudinal direction of the lateral strips of the above knit fabric. The central support of the implant according to the invention can be cut from the central strip of the knit fabric according to the invention.

Thus, the present invention also relates to a method of producing a supporting implant for treating prolapses comprising at least one central support and at least two extending arms extending from this central support, characterized in that it comprises the following steps:
- sourcing a prosthetic knit fabric as hereinabove,
- cutting the said central support from within the central strip of the said knit fabric,
- unravelling or cutting the said extending arms from within the said lateral strips of the said knit fabric, in the longitudinal direction of the said lateral strips.

As a preference, an implant comprising two extending arms will be used in the treatment of a prolapse of the rectocele type.

In one embodiment of the invention, the said implant comprises at least four extending arms. An implant such as this will be particularly useful in the treatment of a prolapse of the cystocele type.

Thus, in one embodiment of the invention, the breaking load of the implant in the longitudinal direction for each extending arm is greater than or equal to 50 N. Preferably, the said breaking load ranges from 70 to 90 N.

In one embodiment of the invention, the elongation at break of the implant in the longitudinal direction for each extending arm ranges from 25% to 70%. Preferably, the said elongation at break ranges from 50% to 70%.

In one embodiment of the invention, the breaking load of the implant in the longitudinal direction of the central support is greater than or equal to 60 N. Preferably, the said breaking load ranges from 70 to 90 N.

In one embodiment of the invention, the elongation at 30 N of the implant in the longitudinal direction of the central support ranges from 30% to 50%. Preferably, the said elongation ranges from 40% to 50%.

In one embodiment of the invention, the central support comprises pores the mean width of which varies from 2.5 mm to 3 mm and the mean height of which varies from 1.6 mm to 1.9 mm. Thus, this central support is particularly flexible, elastic and non-aggressive towards the organ it is intended to support.

In one embodiment of the invention, the said central support is covered on at least one side with a bioresorbable material.

In one embodiment of the invention, the implant further comprises at least one radiopaque yarn. This radiopaque yarn may be chosen from biocompatible metal yarns, biocompatible polymer yarns impregnated with barium sulphate. Examples of biocompatible metal yarns include yarns made of metals chosen from platinum, platinum-iridium, titanium, steel, silver and mixtures thereof.

A yarn such as this allows the surgeon to use X-ray to monitor any movement of the implant once it has been implanted in the patient.

The invention will be better understood from the description which follows, with reference to the attached drawing.

In all of the figures.

AA' defines the longitudinal direction or dimension of the extending arms of the implant;

BB' defines the longitudinal direction or dimension of the central support of the implant;

CC' defines the transverse direction or dimension of the central support of the implant;

EE' defines the longitudinal direction or dimension of the knit fabric, of the central strip of the knit fabric or of the lateral strips of the knit fabric; and FF' defines the transverse direction or dimension of the knit fabric, of the central strip of the knit fabric or of the lateral strips of the knit fabric.

Figure 3:
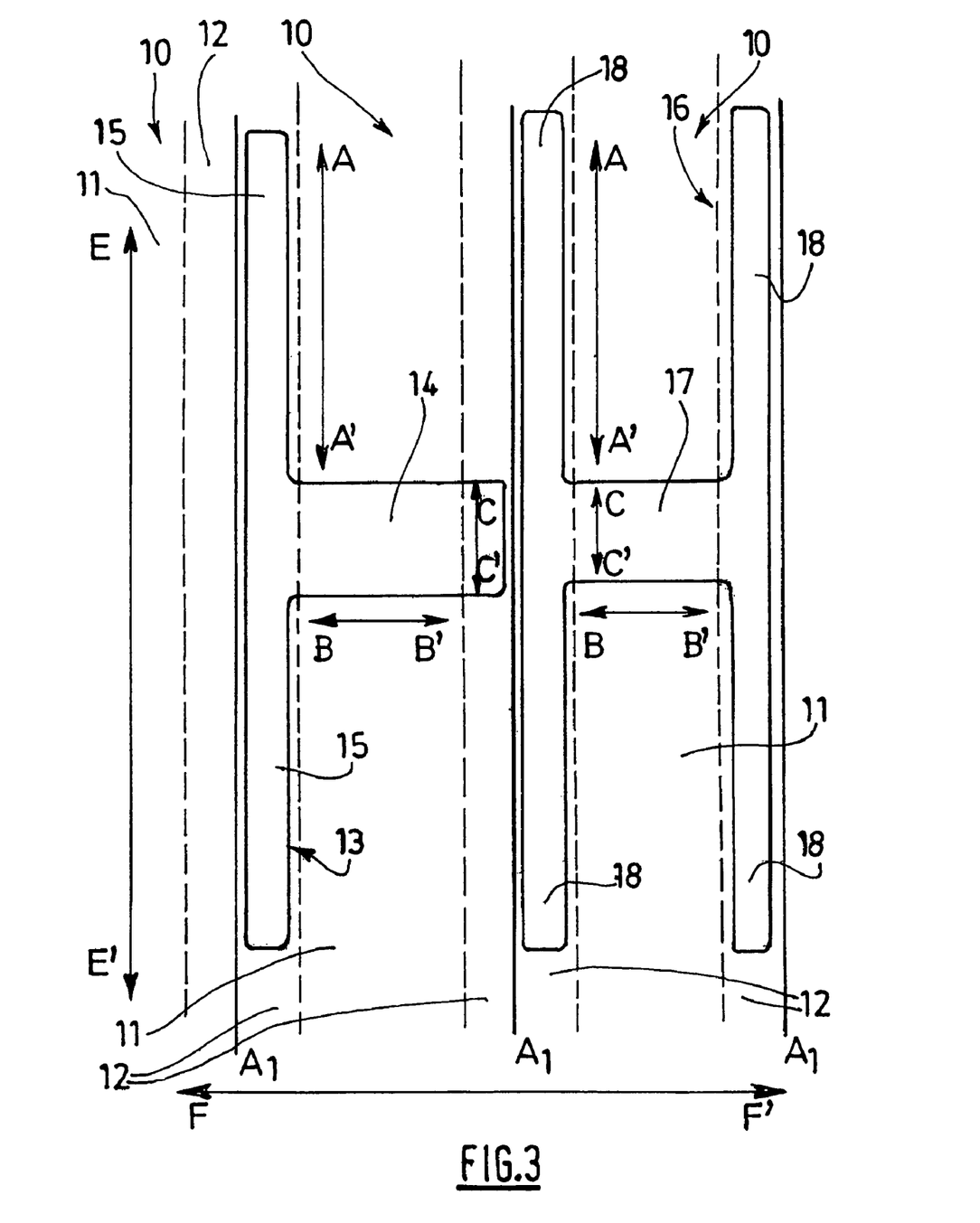
FIG. 3 depicts a prosthetic knit fabric according to the invention, comprising pre-cuts for producing supporting implants for treating prolapses.

Reference is made to FIG. 3 which depicts two prosthetic knits fabric 10 according to the invention knitted side by side on the same knitting machine and partially depicts a third knit fabric 10. The three knits fabric 10 are joined together by an unravellable pillar stitch yarn A1. All that is required to separate two knit fabrics 10 from one another is for the unravellable pillar stitch yarn A1 to be unravelled. The knit fabric edges thus obtained, particularly the exterior edges of the lateral strips 12 or of the extending arms (15, 18) of the implants (13, 16) are scalloped and do not fray.

Each knit fabric 10 comprises a central strip 11 and two lateral strips 12. A lateral strip 12 of a first knit fabric 10 lies adjacent to a lateral strip 12 of a second knit fabric 10, that is adjacent to the first knit fabric 10.

In this FIG. 3, a first knit fabric 10 comprises a cut defining a supporting implant 13 for treating prolapses of the rectocele type. The central support 14 of the implant 13 is cut from the central strip 11 of the knit fabric 10, the extending arms 15 of the implant 13 being cut, or alternatively unravelled, from the two respective lateral strips 12 of the knit fabric. As a preference, as depicted in FIG. 3, on the same side as the extending arms 15, the central support 14 encroaches slightly, for example over a few millimeters, on a lateral strip 12 so as not to create a point of weakness where the central support 14 meets the extending arms 15. On the opposite side to the extending arms 15, the central support 14 is continued across the entirety of the width of the lateral strip 12 to form a reinforced region for possible suturing during placement of the implant 13.

In this FIG. 3, a second knit fabric 10 comprises a cut defining a supporting implant 16 for treating a prolapse of the cystocele type. The central support 17 of the implant 16 is cut from the central strip 11 of the knit 10, the extending arms 18 of the implant 16 being cut, or alternatively unravelled, from the two respective lateral strips 12 of the knit 10. As a preference, as depicted in FIG. 3, the central support 17 encroaches slightly, for example over a few millimeters, on each of the lateral strips 12 so as not to create a point of weakness where the central support 17 meets the extending arms 18.

By virtue of the construction of the prosthetic knit fabric according to the invention, the implants (13, 16) have great flexibility, great porosity and great elasticity in their central support (14, 17) intended to come into contact with the organ that is to be supported, while they exhibit good tensile strength in their respective extending arms (15, 18) intended to be anchored for example in the abdominal wall.

It is equally possible for the prosthetic knit fabric not to have any particular cut. The surgeon can then cut out the particular shape he desires to fashion a supporting implant for treating prolapses, the simple use of the prosthetic knit fabric according to the invention amongst other things making it possible to produce implants and slings of all shapes, even the most complex shapes.

Figure 4:
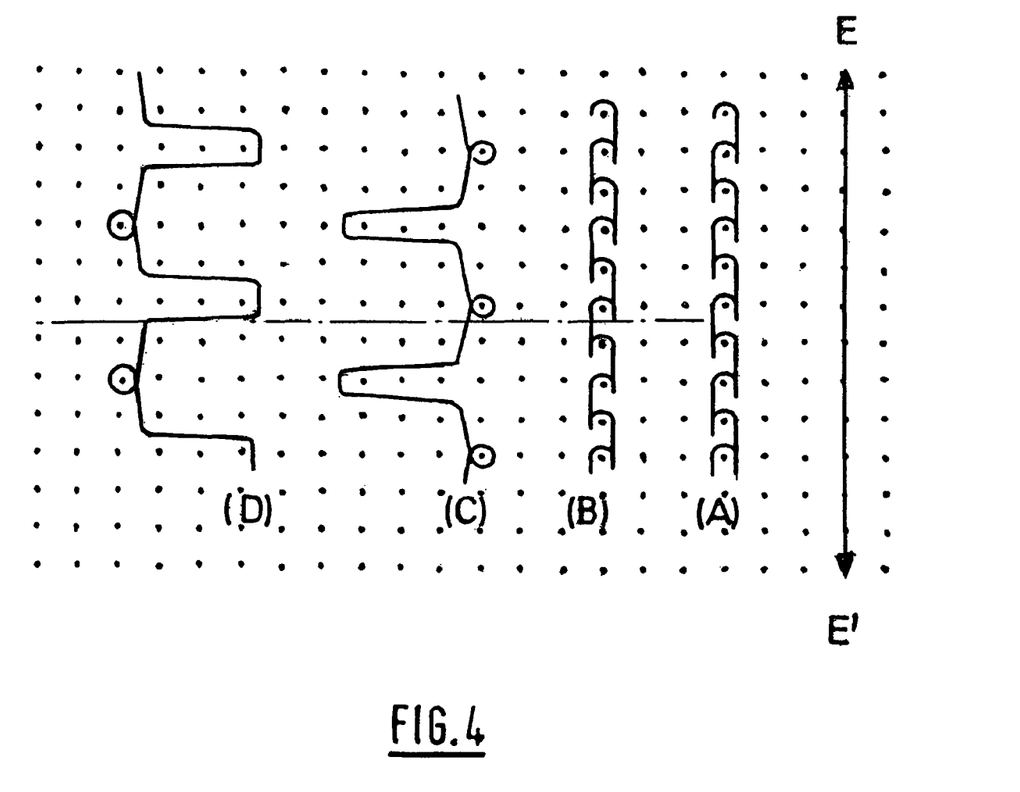
FIG. 4 depicts a schematic diagram of the patterns of a knit fabric according to the invention.

FIG. 4 depicts yarns (A), (B), (C) and (D) that can form sets suitable for producing a prosthetic knit fabric according to the invention.

Thus, the yarns (A) produce a first set of yarns defining a pillar stitch pattern according to the pattern chart: 1-0/0-1//. This first set of yarns extends across the entire surface of the central strip and of the lateral strips of the knit fabric.

For example, for a knit fabric produced on a warp knitting machine or Raschel knitting machine, the first set of yarns is produced on a first guide bar with the following threading diagram: (1 full-1 empty)×31. This threading is distributed according to the following: (1 full-1 empty)×5 on a first lateral strip, (1 full-1 empty)×20 on the central strip, and (1 full-1 empty)×6 on the second lateral strip. This threading diagram corresponds to a pattern repeat, that is to say, with reference to FIG. 3, to a knit pattern contained between two yarns A1, one of the two yarns A1 being comprised in the pattern repeat. n knit fabrics are knitted side by side on the same knitting machine with n pattern repeats. n may, for example, be equal to 19.

Still with reference to FIG. 4, the yarns (B) produce a second set of yarns defining a pillar stitch pattern according to the pattern chart: 1-0/0-1//. This second set of yarns extends only across the width of the lateral strips of the knit fabric.

For example, using the same knitting machine as was used for the first set of yarns, the second set of yarns is produced on a second guide bar with the following threading diagram: (1 empty, 1 full)×5, 40 empty, (1 empty-1 full)×6, the last full being the unravellable yarn A1, multiplied by n pattern repeats. This threading is distributed according to the following: (1 empty, 1 full)×5 on the first lateral strip, the 40 empty on the central strip, and 1 empty-1 full)×6 on the second lateral strip.

Thus, the first set of pillar stitch yarns (A) and the second set of pillar stitch yarns (B) form together a first threading on the width of the central strip, corresponding to (1 full-1 empty)×20. The first set of pillar stitch yarns (A) and the second set of pillar stitch yarns (B) form together a second threading on the width of the lateral strips, said second threading corresponding to 11 full on each lateral strip. The second threading is therefore denser than the first threading: indeed, in the second threading, each eyelet is fed with a yarn, whereas in the first threading, only one eyelet out of two is fed with a yarn.

By virtue of these two different threadings, in particular because of the fact that the second threading is denser than the first threading and thus reinforced with respect to said first threading, the lateral strips show a very good tensile strength in the longitudinal direction EE' of the knit fabric, and the central strip is open and more elastic.

In another embodiment of the invention which has not been depicted, the second set of yarns may be produced on the same guide bar as was used for the first set of yarns, with the threading diagram 10 full, (1 full-1 empty)×20, 12 full, the last full being the unravellable yarn A1, multiplied by n pattern repeats.

In another embodiment of the invention which has not been depicted, a radiopaque yarn may be added, non-stitching, for example according to the pattern chart 1-1/0-0// or the pattern chart 0-0//, and with a threading diagram such that there is, for example, one radiopaque yarn in the middle of each lateral strip and in the middle of the central strip. Any other threading diagram for this radiopaque yarn is also possible.

Still with reference to FIG. 4, the yarns (C) and (D) produce two partial weft stitching sets of a prosthetic knit fabric according to the invention. As appears on this figure, each of the yarns (C) and (D) moves perpendicularly to the longitudinal direction EE' of the knit fabric and forms one stitch every 4 courses.

The yarns (C) produce a first partial weft stitching set on a third guide bar with the following pattern chart and threading diagram:

Pattern chart: 1-0/1-1/4-4/1-1//.

Threading diagram: 2 empty, (1 full-1 empty)×30 multiplied by n pattern repeats.

The yarns (D) produce a second partial weft stitching set on a fourth guide bar with the following pattern chart and threading diagram:

Pattern chart: 0-0/3-3/3-4/3-3//.

Threading diagram: 1 full, 3 empty, (1 full-1 empty)×29 multiplied by n pattern repeats.

These two partial weft stitching sets extend across the entire surface of the central strip and of the lateral strips of the knit fabric.

Thus, across the width of the lateral strips of the knit fabric, the knit fabric comprises two sets of yarns defining pillar stitch patterns. The mechanical strength of the lateral strips in the longitudinal direction is thus particularly high.

By contrast, on the part of the central strip of the knit fabric there is just one set of yarns defining a pillar stitch pattern. On the central strip, there are also the two sets of partial weft stitching yarns. Thus, this central strip is stabilized in its longitudinal and transverse directions. It is less dense than the lateral strips and more open. It is also more elastic.

The loom-finished knit fabric obtained is preferably subjected to a heat-setting operation which further improves its stabilization in the longitudinal and transverse directions.

Implants according to the invention as shown in FIG. 3 can be cut from a prosthetic knit fabric as obtained with the patterns described in FIG. 4.

The patterns described in FIG. 4 and the threading diagrams described hereinabove also allow the lateral strips to be unravelled according to the method described in applications WO 2006/111664 and WO 2006/111665. Thus, it is possible to obtain implants in which the edges of the extending arms are scalloped, as described in WO 2006/111664 and WO 2006/111665.

EXAMPLE

A knit fabric was produced according to the invention from a monofilament polypropylene yarn of a diameter of 0.10 mm, on a warp knitting machine, using the following pattern charts for the various sets, and with reference to FIG. 4:

first set of pillar stitch pattern (yarns A): 1-0:0-1//,
second set of pillar stitch pattern (yarns B): 1-0:0-1//,
first partial weft stitching set (yarns C): 1-0/1-1/4-4/1-1//,
second partial weft stitching set (yarns D):0-0/3-3/3-4/3-3//.

The guide bars for the various sets were threaded in the following threading diagrams:

Yarns A: (1 full-1 empty)×31
Yarns B: (1 empty, 1 full)×5, 40 empty, (1 empty-1 full)×6
Yarns C: 2 empty, (1 full-1 empty)×30
Yarns D: 1 full, 3 empty, (1 full-1 empty)×29

These threading diagrams were repeated n times, for example 19 times, to form n, for example 19, pattern repeats.

The loom-finished knit fabric was subjected to a heat-setting operation.

With reference to FIG. 3, the width of the central strip 11 was 5 cm. The width of each lateral strip 12 was 1 cm. An implant 13 was cut out from this knit fabric for treating a prolapse of the rectocele type, by cutting a central support 14 with the overall shape of a quadrilateral from the central strip 11 and cutting two extending arms 15 from the same lateral strip 12.

The breaking load and the elongation at break of the extending arms were then measured in their longitudinal direction AA'. The results were as follows:

breaking load in the longitudinal direction of an extending arm, measured in accordance with ISO 13934-1 for which the width of the test specimen was 1 cm and the length of the test specimen was 100 mm: 90 N,
elongation at break in the longitudinal direction of an extending arm, measured in accordance with ISO 13934-1 for which the width of the test specimen was 1 cm and the length of the test specimen was 100 mm: 65%.

The extending arm thus cut from a lateral strip of the knit according to the invention has excellent tensile strength and limited extensibility. It is thus entirely suited to the production of a supporting implant for treating prolapses.

The breaking load and the elongation were also measured on the central support under a load of 30 N in its longitudinal direction BB'. The results obtained were as follows:
- breaking load in the longitudinal direction of the central support, measured in accordance with ISO 13934-1 for which the width of the test specimen was 40 mm and the length of the test specimen was 60 mm: 85 N,
- elongation at 30 N in the longitudinal direction of the central support, measured in accordance with ISO 13934-1 for which the width of the test specimen was 40 mm and the length of the test specimen was 60 mm: 45%.

The central support thus exhibits excellent elasticity.

The present invention is not restricted to the embodiments described by way of examples in this application. For example, the width of the central strip and that of the lateral strips may vary, for example by varying the threading diagrams of the set or sets of pillar stitch yarns.

In another embodiment of the invention, the central strip 11 of the prosthetic knit fabric is covered on at least one side with a bioresorbable material, for example collagen, the implant thus being particularly non-aggressive towards the organ that is to be supported.

The invention claimed is:

1. A prosthetic open knit fabric made as a single piece, comprising, a central strip and two lateral strips, one lateral strip on each side of the central strip, characterized in that the fabric comprises a first and second set of pillar stitch yarns defining a pillar stitch pattern in a longitudinal direction and at least two partial weft stitching sets of yarns that move perpendicular to the longitudinal direction, the first set of pillar stitch yarns extending entirely across a width of the central strip and of the lateral strips and the second set of pillar stitch yarns extending only across a width of the lateral strips, together forming a first threading across the width of the central strip and a second threading across the width of the lateral strips.

2. The prosthetic open knit fabric according to claim 1, characterized in that the second threading is denser than the first threading.

3. The prosthetic open knit fabric according to claim 1, characterized in that the at least two partial well stitching sets of yarns extend across the entire width of the central strip and of the lateral strips of the knit fabric.

4. The prosthetic open knit fabric according to claim 1, characterized in that a breaking load of the knit fabric in the longitudinal direction for each lateral strip is greater than or equal to 50 N.

5. The prosthetic open knit fabric according to claim 4, characterized in that the said breaking load ranges from 70 to 90 N.

6. The prosthetic open knit fabric according to claim 1, characterized in that an elongation at break of the knit fabric in the longitudinal direction for each lateral strip ranges from 25% to 70%.

7. The prosthetic open knit fabric according to claim 6, characterized in that the elongation at break ranges from 50% to 70%.

8. The prosthetic open knit fabric according to claim 1, characterized in that a breaking load of the knit fabric in a transverse direction for the central strip is greater than or equal to 60 N.

9. The prosthetic open knit fabric according to claim 8, characterized in that the breaking load ranges from 70 to 90 N.

10. The prosthetic open knit fabric according to claim 1, characterized in that an elongation at 30 N of the knit fabric in a transverse direction for the central strip ranges from 30% to 50%.

11. The prosthetic open knit fabric according to claim 10, characterized in that the elongation ranges from 40% to 50%.

12. The prosthetic open knit fabric according to claim 1, characterized in that the central strip comprises pores a mean width of which varies from 2.5 mm to 3 mm and a mean height of which varies from 1.6 mm to 1.9 mm.

13. The prosthetic open knit fabric according to claim 1, characterized in that the knit is produced from yarns, monofilaments or multifilaments of a biocompatible polymer material chosen from polypropylene, polyester, polyamide and blends thereof.

14. The prosthetic open knit fabric according to claim 1, characterized in that the central strip is covered on at least one side with a bioresorbable material.

15. The prosthetic open knit fabric according to claim 1, characterized in that the knit further comprises at least one radiopaque yarn.

16. A method of producing a prosthetic open knit fabric made as a single piece, comprising, a central strip and two lateral strips, one lateral strip on each side of the central strip, characterized in that the method comprises the following step: producing a knit fabric on a warp knitting machine or Raschel knitting machine using a first and second set of pillar stitch yarns defining a pillar stitch pattern in a longitudinal direction and at least two partial weft stitching sets of yarns that move perpendicular to the longitudinal direction, the first and second set of pillar stitch yarns being threaded continuously or partly threaded across an entire width of the lateral strips and of the central strip on one or more guide bar(s) and together forming a first threading across the width of the central strip and a second threading across the width of the lateral strips.

17. The method according to claim 16, characterized in that the first set of pillar stitch yarns are threaded continuously along a first guide bar across the entire width of the lateral strips and of the central strip and the second set of pillar stitch yarns are partly threaded on a second guide bar across only the width of each of the lateral strips.

18. The method according to claim 16, characterized in that, when the width of the warp knitting machine or Raschel knitting machine allows several knit fabrics to be knitted side by side, a lateral strip of a first knit fabric lies adjacent to a lateral strip of a second knit fabric so the partial weft stitching sets of the said first and second knit fabrics have a pattern such that for any pillar stitch yarn separating two adjacent lateral strips, any weft yarn of the said partial well stitching sets approaching the said pillar stitch yarn makes a U-turn at this pillar stitch yarn.

19. A supporting implant for treating prolapses, obtained by unravelling the pillar stitch yarns of knit fabrics obtained according to claim 18 and cutting the central strip of the said knit fabric or knit fabrics.

20. A method of producing a supporting implant for treating prolapses comprising at least one central support and at least two extending arms extending from this central support, characterized in that the method comprises the following steps: sourcing a prosthetic knit fabric according to claim 1, cutting a central support from within the central strip of the knit fabric, unravelling or cutting extending arms from within the lateral strips of the knit fabric, in the longitudinal direction of the lateral strips.

21. A supporting implant obtained according to claim 20, characterized in that the knit comprises at least four extending arms.

22. A supporting implant according to claim 20, characterized in that a breaking load of the implant in the longitudinal direction for each extending arm is greater than or equal to 50 N.

23. A supporting implant according to claim 22, characterized in that the breaking load ranges from 70 to 90 N.

24. A supporting implant according to claim 20, characterized in that an elongation at break of the implant in the longitudinal direction for each extending arm ranges from 25% to 70%.

25. A supporting implant according to claim 24, characterized in that the elongation at break ranges from 50% to 70%.

26. A supporting implant according to claim 20, characterized in that a breaking load of the implant in the longitudinal direction of the central support is greater than or equal to 60 N.

27. A supporting implant according to claim 26, characterized in that the breaking load ranges from 70 to 90 N.

28. A supporting implant according to claim 20, characterized in that an elongation at 30 N of the implant in the longitudinal direction of the central support ranges from 30% to 50%.

29. A supporting implant according to claim 28, characterized in that the elongation ranges from 40% to 50%.

30. A supporting implant according to claim 20, characterized in that the central support comprises pores a mean width of which varies from 2.5 mm to 3 mm and a mean height of which varies from 1.6 mm to 1.9 mm.

31. A supporting implant according to claim 20, characterized in that the central support is covered on at least one side with a bioresorbable material.

32. A supporting implant according to claim 20, characterized in that the implant further comprises at least one radiopaque yarn.

* * * * *